United States Patent [19]

Plocharczyk et al.

[11] Patent Number: 5,374,719
[45] Date of Patent: Dec. 20, 1994

[54] PROCESS FOR CONVERTING LORACARBEF DIHYDRATE TO LORACARBEF MONOHYDRATE

[75] Inventors: Edward F. Plocharczyk, Zionsville; Erin E. Strouse, Indianapolis, both of Ind.

[73] Assignee: Eli Lilly and Company, Indianapolis, Ind.

[21] Appl. No.: 71,550

[22] Filed: Jun. 4, 1993

[51] Int. Cl.$^5$ .................................. C07D 487/04
[52] U.S. Cl. ......................................... 540/205
[58] Field of Search ............... 540/215, 230, 222, 228, 540/205

[56] References Cited

U.S. PATENT DOCUMENTS 3,502,663  3/1970  Barnes .
3,531,481  9/1970  Pfeiffer .
4,977,257 12/1990  Eckrich et al. .

FOREIGN PATENT DOCUMENTS 0311366 10/1988  European Pat. Off. .
0369686 11/1989  European Pat. Off. .

*Primary Examiner*—Nicholas Rizzo
*Attorney, Agent, or Firm*—Thomas G. Plant; Gerald V. Dahling; James J. Sales

[57] ABSTRACT

A process for the preparation of the crystalline monohydrate form of the compound of formula (I)

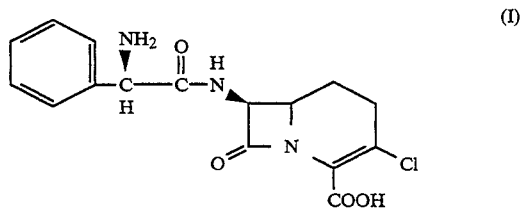

which includes exposing the crystalline dihydrate form of the compound of formula (I) to a temperature of between about 50° and 65° C. and a relative humidity of between about 60 to a about 100%.

3 Claims, No Drawings

PROCESS FOR CONVERTING LORACARBEF DIHYDRATE TO LORACARBEF MONOHYDRATE

BACKGROUND OF THE INVENTION

This invention relates to a process for the preparation of crystalline loracarbef monohydrate.

The β-lactam antibiotic of the formula (I)

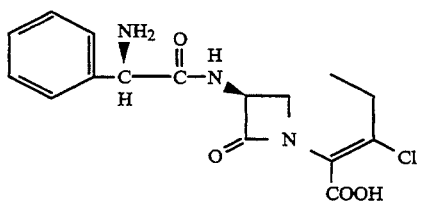

is the potent orally active antibiotic known as loracarbef. The antibiotic is described, for example, by Hashimoto et al. in U.S. Pat. No. 4,335,211, issued Jun. 15, 1982.

The above compound is known in various forms, including the crystalline monohydrate form, which is disclosed in European Patent Publication 0,311,366 having a publication date of Apr.12, 1989. Other known solvate forms of the compound are disclosed in Eckrich et al. U.S. Pat. No. 4,977,257. The crystalline dihydrate form of loracarbef is disclosed in European Patent Publication 0,369,686 having a publication date of May 23, 1990. As indicated in the EPO application, the crystalline monohydrate may be prepared by first suspending the dihydrate in water and effecting solution by the addition of acid followed by the adjustment of the pH with base, or by the addition of base followed by acid.

It has been determined that loracarbef crystalline monohydrate is a fine "hair-like" crystal which results in very slow filtration. In filtering the monohydrate, the crystals tend to form a mat on the filter medium which prevents or reduces the ability to de-water the filter cake, which increases the wash volume required As loracarbef monohydrate is moderately soluble in water, (approximately 10 mg/ml), loss of yield results when such washes are increased. Total filtration time is of course increased as wash volume increases.

What is needed in light of the above difficulties is a process for preparing crystalline loracarbef monohydrate in a more efficient manner, that is, avoid the requirement of filtering the crystalline monohydrate.

SUMMARY OF THE INVENTION

The invention provides a process for the preparation of the crystalline monohydrate form of the compound of formula (I)

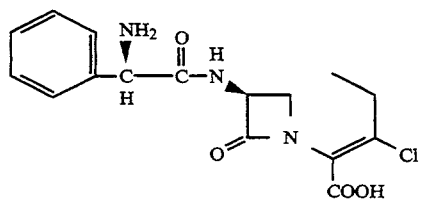

which comprises exposing the crystalline dihydrate form of a compound of formula (i) to a temperature between about 50° to about 65° C. and a relative humidity of between about to about 100%.

DESCRIPTION OF THE INVENTION

Loracarbef dihydrate exists in a plate-like habit and consequently filters much more quickly than the crystalline monohydrate form of loracarbef. Experimentation has shown that this filtration may be 20 times as fast as the filtration of the monohydrate. Attempts have been made to convert dihydrate to monohydrate a wet cake or dry solid using high temperatures alone. However, that procedure proved unsuccessful.

It was discovered that using a high relative humidity in combination with high temperatures produced a solid state conversion from dihydrate to monohydrate. This discovery provided a process to avoid isolation of the monohydrate through filtration, as the monohydrate may be isolated through forming the easily filtered dihydrate, which then may undergo the solid state conversion to the monohydrate. Also, there is no need to crystallize the monohydrate from solution using acid or base, as described previously.

The solid state conversion from dihydrate to monohydrate takes place in an environment of both elevated temperature, from about 50° to about 65° C., and at high relative humidities, from about 60 to about 100%. While other forms of loracarbef were used in such a process, it has been found that the dihydrate form surprisingly converts exclusively to the monohydrate. Other solvate forms such as the bis(DHF)solvate and the ethanolate, which were exposed to various combinations of temperatures and relative humidities converted to non-monohydrate forms or a mixture of forms. Therefore, the invention also provides for a conversion of the dihydrate crystal form exclusively to the monohydrate crystal form.

The dihydrate can be prepared through means known in the art, such as taught in the European Patent Publication 369,686, previously referenced. The dihydrate may be in the form of a wet cake or a dry powder. The dihydrate is placed in an uncovered container, and thereafter placed in a humidity cabinet having a relative humidity of 60–100%, at a temperature of about 50° to about 65° C. A prefered humidity range is between about 80 to about 90%, and a preferred temperature range is between about 50° to about 60° C. The dehydrate is left at these conditions for several hours, and it is noted that in some experiments the conversion to the monohydrate at a temperature of 60° C. and relative humidity of 90% occurred in under 8 hours. The conversion can be monitored via microscopic observation and when the material appears microscopically to have converted to the monohydrate, samples may be taken and sent for Karl Fischer and X-ray diffraction pattern assays for confirmation of composition. It is believed that the conversion is a solid to solid transformation, rather than a dissolution followed by a recrystallization. This is surprising as there is a net loss of water in a wet environment.

Microscopically, the crystals could be seen changing from plates of dehydrate to the needles of monohydrate during the conversion. The Karl Fischer values changed from 9% to 5%, coinciding with the change from dehydrate to monohydrate. The X-ray diffraction patterns of the resulting materials had a pattern identical to that of the monohydrate reference pattern. Also, no new peaks observed, so the dehydrate is shown to convert exclusively to monohydrate.

EXPERIMENTAL SECTION

Example 1

Loracarbef dehydrate (5 g, starting KF=9.3%), was placed in a petri dish and then placed in humidity cabinet at 60% relative humidity and 20° C. It was left at that setting for 24 hours, and monitored via microscopic observations. No changes were seen, so that temperature was increased by 10°, and again left for 24 hours. This process was repeated until the temperature reached 60° C. No monohydrate growth took place until the temperature reached 50° C., and at 60° C. much more monohydrate was visible. The X-ray patterns showed that at 50° C., mostly dehydrate remained, but at 60° C., the patterns showed primarily monohydrate with a trace of dehydrate left. The KF assays showed a decrease in water content after the material was held at 60° C.

Example 2

Loracarbef dehydrate (3 g) was placed in a petri dish, and the open container placed in a humidity cabinet at 60° C., and 80% relative humidity. After 2 hours the material looked largely like monohydrate as seen through the microscope. The X-ray pattern confirmed the conversion, showing mostly monohydrate with a small amount of dehydrate remaining.

Example 3

Loracarbef dehydrate (5 g, starting KF=8.7%), was placed in a petri dish and then placed in a humidity cabinet at 60° C. and 80% relative humidity. Conversion was monitored via microscopic observation and after 72 hours the material appeared to be primarily monohydrate. The product had a KF=5.5%, the amount of total related substances was 0.51%, and the potency was 96.5%. The X-ray pattern confirmed the material to be monohydrate.

Example 4

A 500 ml one neck glass Parr Bottle was equipped with a rubber stopper, and two concentric tubes. The tubes provided a path to supply and remove nitrogen saturated with water vapor to the inside of the bottle. The end of each tube was sealed, and a hole was drilled in the tubing wall; this provided volume for a water trap if any water vapor were to condense in these lines. Loracarbef dihydrate (approximately 0.75 grams) was spread evenly on the bottom of the Parr Bottle, and the bottle was tightly stoppered. The Parr Bottle was then submerged in a 4 liter Resin Flask filled with water. The resin flask was equipped with a heating mantle and temperature controller, set to 65° C. In addition, dry nitrogen was sparged into the water through a sintered metal frit at a controlled rate of 100 sccm/min; this provided a nitrogen stream saturated with water vapor at the temperature of the water and submerged Parr Bottle. The resin flask and Parr bottle tubing were sealed and connected so that the 100 sccm/min of nitrogen had to vent by sweeping through the Parr bottle. The dehydrate loaded into the Par bottle assayed at 8.9 wt % $H_2O$ by KF titration. Visual observation with an optical microscope indicated a plate crystal habit characteristic of the dehydrate crystal form. After exposing the dehydrate to 65° C. with 100 sccm/min of nitrogen saturated with water vapor (100% relative humidity) for 70 hours, the material in the Parr bottle was removed. Visual observation with an optical microscope indicated a needle crystal habit characteristic of the monohydrate crystal form. The KF titration indicated the crystals were 5.5 Wt % $H_2O$.

We claim:

1. A process for the preparation of the crystalline monohydrate form of the compound of formula (I)

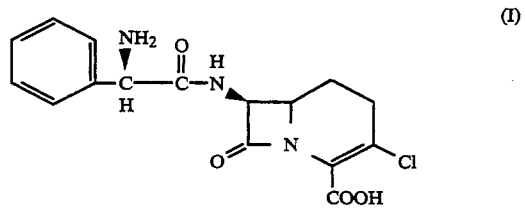

which comprises exposing the crystalline dehydrate form of the compound of formula (I) to a temperature of between about 50° to about 65° C. and a relative humidity of between about 60 to about 100%.

2. The process as recited in claim 1 wherein said relative humidity is between about 80 to about 90%.

3. The process as recited in claim 2 wherein said temperature is between about 50° to about 60° C.

* * * * *

UNITED STATES PATENT AND TRADEMARK OFFICE
CERTIFICATE OF CORRECTION

PATENT NO. : 5,374,719                  Page 1 of 2
DATED       : December 20, 1994
INVENTOR(S) : Plocharczyk, Edward F. and Strouse, Erin E.

It is certified that error appears in the above-indentified patent and that said Letters Patent is hereby corrected as shown below:

Column 1, line 50 "that is, avoid" should read -- that is, to avoid --.

Column 2, line 10 "monohydrate a wet cake" should read -- monohydrate as a wet cake --.

Column 2, line 61 "dehydrate" should read -- dihydrate --.

Column 2, line 64 "dehydrate" should read -- dihydrate --.

Column 2, line 67 "new peaks observed, so the dehydrate" should read -- new peaks are observed, so the dihydrate --.

Column 3, line  4 "dehydrate" should read -- dihydrate --.

Column 3, line 14 "dehydrate" should read -- dihydrate --.

Column 3, line 16 "dehydrate" should read -- dihydrate --.

Column 3, line 22 "dehydrate" should read -- dihydrate --.

Column 3, line 28 "dehydrate" should read -- dihydrate --.

Column 3, line 31 "dehydrate" should read -- dihydrate --.

UNITED STATES PATENT AND TRADEMARK OFFICE
CERTIFICATE OF CORRECTION

PATENT NO. : 5,374,719
DATED : December 20, 1994
INVENTOR(S) : Plocharczyk, Edward F. and Strouse, Erin E.

It is certified that error appears in the above-indentified patent and that said Letters Patent is hereby corrected as shown below:

Column 4, line 17 "dehydrate" should read -- dihydrate --.

Column 4, line 18 "dehydrate" should read -- dihydrate --.

Column 4, line 39 "dehydrate" should read -- dihydrate --.
Column 4, line 14, "dehydrate" should read --dihydrate --.

Signed and Sealed this

Third Day of October, 1995

Attest:

BRUCE LEHMAN

*Attesting Officer*   Commissioner of Patents and Trademarks